United States Patent [19]
Imbert et al.

[11] Patent Number: 6,008,382
[45] Date of Patent: Dec. 28, 1999

[54] METHOD FOR PREPARING 4'-DEMETHYLEPIPODOPHYLLOTOXIN FROM PODOPHYLLOTOXIN

[75] Inventors: Thierry Imbert, Viviers-les-Montagnes; Yves Guminski, Lagarrigue, both of France

[73] Assignee: Pierre Fabre Medicament, Boulogne, France

[21] Appl. No.: 09/077,303

[22] PCT Filed: Dec. 13, 1996

[86] PCT No.: PCT/FR96/02000

§ 371 Date: Jun. 12, 1998

§ 102(e) Date: Jun. 12, 1998

[87] PCT Pub. No.: WO97/21713

PCT Pub. Date: Jun. 19, 1997

[30] Foreign Application Priority Data

Dec. 14, 1995 [FR] France ................................. 95 14875

[51] Int. Cl.⁶ .................................................. C07D 307/77
[52] U.S. Cl. .................................................. 549/298
[58] Field of Search .............................. 549/298

[56] References Cited

FOREIGN PATENT DOCUMENTS 90 09788   7/1990   WIPO .

OTHER PUBLICATIONS

N Fujii et al, J Chem Soc, Perkin Transaction 1 (1977) pp. 2288–2289.
H Irie et al, Chemistry Letters (1980) pp. 875–878.
J Kunitomo et al, Heterocycles, 34(5) (1992) pp. 937–942.
J Andre et al, Chem Abs 117(23) (1992) No. 234312q.
M Kuhn et al, Helvetica Chimica Acta 52(4) (1969) pp. 944–947.
L Thurston et al, J Med Chem 29 (1986) pp. 1547–1550.
H Hansen et al, Acta Chemica Scandinavica 47 (1993) pp. 1190–1200.
H Saito et al, Chemistry Letters (1987) pp. 799–802.

*Primary Examiner*—Amelia Owens
*Attorney, Agent, or Firm*—The Firm of Gordon W. Hueschen

[57] ABSTRACT

A method for synthesizing a 4'-demethylepipodophyllotoxin of formula (II) from a podophyllotoxin of formula (I) by treating it with a pair of reagents, i.e. a strong acid and an aliphatic, aromatic or functionalized sulphide, in the present of an organic or inorganic acid, or in the presence of water with or without a water-miscible organic solvent.

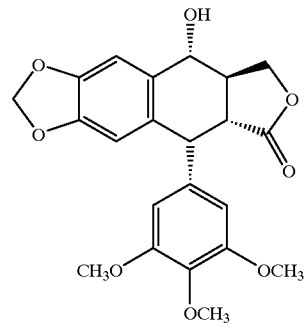

I

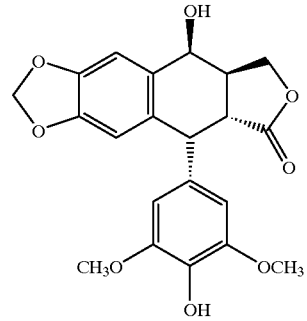

II

6 Claims, No Drawings

METHOD FOR PREPARING 4'-DEMETHYLEPIPODOPHYLLOTOXIN FROM PODOPHYLLOTOXIN

The present application is a U.S. National Application filed under 35 USC 371 of PCT/FR96/02000, filed Dec. 13, 1996 based upon French application Serial No. 95/14875 filed Dec. 14, 1995.

The present invention relates to a novel method for the demethylation of podophyllotoxin I in order to access 4'-demethylepipodophyllotoxin of formula II

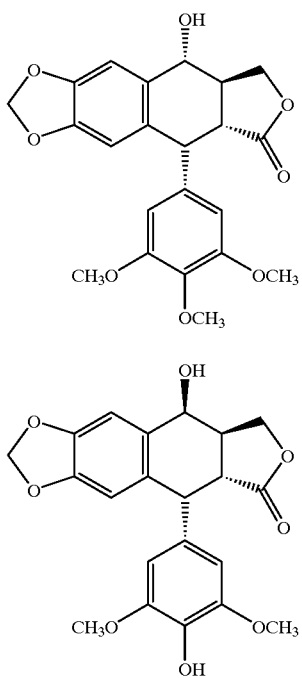

4'-Demethylepipodophyllotoxin is a key synthetic intermediate in the preparation of novel anticancer substances, of which mention may be made, for example, of etoposide and teniposide.

The preparation of 4'-demethylepipodophyllotoxin II is known and is usually carried out by demethylation of podophyllotoxin I by HBr, according to the original method described by M. Kuhn, Helvetica Chimica Acta, 1969, 52, 944, and then taken up by several groups, such as K. H. Lee, J. Med. Chem., 1986, 29, 1547 and Journal of Natural Products, 1989, 52, 606, O. Buchardt, Acta Chemica Scandinavica, 1993, 47, 1190 or Y. Nishimura, Chemistry Letters, 1987, 799. This method gives moderate yields, according to the amounts involved, and is relatively difficult to carry out, because of the handling of highly aggressive gaseous HBr. Other methods can be envisaged for carrying out this demethylation, by using the usual reagents for such a conversion: mention may be made of $BBr_3$ or $BCl_3$ in $CH_2Cl_2$ from $-20°$ C. to $+20°$ C. (Tet., 1969, 24, 2289); $AlCl_3$ in $CH_2Cl_2$ at $0°$ C. or at ordinary temperature (according to J. Chem. Soc., 1944, 330); pyridinium hydrochloride at more or less high temperature; $AlBr_3$ in the presence of ethanethiol at ordinary temperature.

These various methods result in the degradation or in the non-conversion of podophyllotoxin.

A novel demethylation method has therefore been developed.

The method which is the subject-matter of the present invention consists in treating podophyllotoxin I with the pair of reagents: strong acid-aliphatic, aromatic or functionalized sulfide, in the presence of an organic or inorganic acid or else in the presence of water, with or without water-miscible organic solvent, such as the acetone-water mixture, advantageously, at a temperature of between $-20°$ C. and $+40°$ C.

According to the specific characteristics of the present invention, the strong acid of the pair of reagents is advantageously composed of methanesulfonic acid, whereas the aliphatic, aromatic or functionalized sulfide of the pair of reagents is advantageously chosen from dimethyl sulfides D,L-methionine and methylthioacetic acid.

According to other advantageous characteristics of the method of the invention, the reaction is carried out in the presence of an organic acid of formula RCOOH, where R=H, $C_1$–$C_4$ alkyl or $CX_3$, with X=Cl or F. It will relate in particular to formic acid or trifluoroacetic acid.

In the case where the reaction is carried out in the presence of an inorganic acid, use can advantageously be made of $H_3PO_4$ or a slight stream of HCl or HBr sparging into the reaction mixture.

In accordance with the present invention, the compound II directly resulting from the reaction is isolated and purified by recrystallization from a solvent, such as isopropyl alcohol, acetic acid, water, acetone, dioxane, isopropyl ether, toluene, ethanol and their mixture.

D,L-Methionine can also be replaced by an aliphatic or aromatic sulfide with a low carbon number or with a functionalized sulfide, for example functionalized by an acidic functional group, such as methylthioacetic acid. In this case, the joint presence of an inorganic or organic acid is no longer necessarily indispensable.

It is known in the chemical literature that the methanesulfonic acid, D,L-methionine pair can demethylate the aromatic methoxy of certain compounds, in order to result in the corresponding phenols: see J. C. S., Perkin Trans. I, 1977, 2288; J. C. S. Chem. Comm., 1976, 922; Chem. Lett., 1980, 875; J. Med. Chem., 1984, 27, 28; Heterocycles, 1992, 34, 937; Synth. Comm., 1992, 22 (16), 2313. One of the reaction products is thus the methylsulfonium derivative of methionine, which means that an aliphatic or aryl sulfide can also be used as demethylation reagent, resulting in the corresponding sulfonium: see, in this respect: M. Julia, Tet. Let., 1979, No. 13, 1101.

It appears that this demethylation method, applied to podophyllotoxin I, only results in decomposition products and consequently cannot be used.

In contrast, if the operation is carried out in the presence of an organic acid as indicated above and in particular formic acid, acetic acid or trifluoroacetic acid or in the presence of an inorganic acid, in particular phosphoric acid, or in the presence of a water-miscible organic solvent, such as the acetone-water mixture, it is possible to selectively demethylate the methoxy in the 4'-position and to obtain the desired product with a good yield.

The inorganic acid can also be gaseous hydrochloric or hydrobromic acid; it is thus possible to use this method, methanesulfonic acid, D,L-methionine on podopyllotoxin I, where the alcohol functional group in the 4-position would have been easily converted beforehand under mild conditions, by virtue of this slight stream of hydrochloric or hydrobromic gas, to halide, Cl or Br, these operations being carried out in a "one pot" process, with the treatment with methanesulfonic acid and methionine; these processes are described in the examples hereinbelow. This operation of gentle treatment with gaseous Hbr is not capable of demethylating the aromatic methoxy in the 4'-position and only uses a very small amount of gas and for a very short time, with respect to the prior process.

The advantage of this method is its simplicity of operation and the purity of the reaction mixture obtained with respect to the prior method, not requiring the handling of large amounts of aggressive gases and specific equipment.

The yields of this demethylation to 4'-demethylepipodophyllotoxin are improved with respect to the prior art. This process can be applied on an industrial scale without particular difficulties by increasing the amounts of substance involved, without loss of yield.

Furthermore, an additional improvement in the process lies in the fact that it is not necessary to purify the compound obtained by column chromatography, which is a lengthy and expensive operation. It is possible, at the end of the reaction, to precipitate the product formed from water and ice, in order to obtain a crystalline product which can be filtered off and recrystallized from solvents, such as, for example, isopropanol, isopropyl ether, acetone, acetic acid or water and their mixture. It is also possible, at the end of the reaction, to extract the product with normal solvents to crystallize and recrystallize the evaporation residue from the abovementioned solvents. The reaction product can be used crude, even without recrystallization, in subsequent synthetic stages, such as, for example, the protection of the phenol in the 4'-position by benzyloxycarbonyl chloride.

The following examples illustrate the various procedures used for this demethylation:

| Example | Starting material | Reagents | Temperature | Time | Yield |
|---|---|---|---|---|---|
| 1 | 1 | 5 g $CH_3SO_3H$ (20 eq) D,L-methionine (1.1 eq) | Ordinary temperature | — | Degradation |
| 2 | 1 | 12 g $CH_3SO_3H$ (45 eq) D,L-methionine (5 eq) $CF_3CO_2H$ (6 eq) | 40° C. | 0.75 h | 93% |
| 2a | 1 | 100 g $CH_3SO_3H$ (45 eq) D,L-methionine (5.5 eq) $CF_3CO_2H$ (10 eq) | 0° C. to 10–20° C. | 1 h | 65% |
| 3 | 1 | 7 g $CH_3SO_3H$ (37 eq) D,L-methionine (8 eq) $HCO_2H$ (4.5 eq) | 40° C. | 25 min | Crystallized yield: 48% Chromato yield: 48% |
| 4 | 1 | 5 g $CH_3SO_3H$ (50 eq) D,L-methionine (6 eq) $H_3PO_4$ | 0° C., then return to ordinary temperature | 6 h | 70% |
| 5 | 1 | 1 g $CH_3SO_3H$ (32 eq) D,L-methionine (1.5 eq) HCl gas | –10° C. | 1 h | 52% |
| 6 | 1 | 50 g $CH_3SO_3H$ (64 eq) D,L-methionine (5.5 eq) Acetone-water 5/1 | 40° C. and return to ordinary temperature | 2 h | 80% |
| 7 | 1 | 5 g $CH_3SO_3H$ (20 eq) D,L-methionine (2 eq) Hbr gas | –10° C. | 2 h | 54% |

Preparation of 4'-demethylepipodophyllotoxin II

The podophyllotoxin used has a natural origin and exhibits a purity of 95%.

EXAMPLE 1

According to H. Yajima, *J. C. S., Perkin I*, 1977, 2288

1 g (2.4 mmol) of podophyllotoxin I are reacted with stirring with 400 mg (2.64 mmol) of D,L-methionine and 3.1 ml (48 mmol) of methanesulfonic acid at ordinary temperature. The mixture immediately turns dark red in color. The degradation of the starting material is observed by TLC.

EXAMPLE 2

Use of Trifluoroacetic Acid 12 g (29 mmol) of podophyllotoxin I are dissolved in 20 ml of trifluoroacetic acid and stirred at room temperature. 21.6 g (0.14 mol) of D,L-methionine and 84 ml (1.29 mol) of methanesulfonic acid are introduced, the temperature rises to 40° C. and stirring is maintained for 45 min. The reaction mixture is then plunged into 500 ml of a mixture of equal volumes of acetone and ice-cold water. Neutralization is carried out with stirring to pH 4 to 5 by addition of $K_2CO_3$ and then extraction is carried out twice with ethyl acetate, the organic phases are dried over $Na_2SO_4$ and filtered, and the solvent is evaporated under reduced pressure. The evaporation residue crystallizes from isopropyl ether, 10.7 g, Yd 93%.

The 4'-demethylepipodophyllotoxin obtained according to this process can afterwards be used directly in subsequent reactions, such as the protection of the phenol in the 4'-position by benzyloxycarbonyl chloride.

EXAMPLE 2a

Use of Trifluoroacetic Acid 100 g (0.24 mol) of podophyllotoxin I are dissolved in 186 ml of trifluoroacetic acid with stirring. After cooling the reaction mixture to 0° C., a solution of 198 g (1.32 mol) of D,L-methionine in 500 ml of methanesulfonic acid is introduced, the reaction mixture being maintained between 10 and 20° C. 200 ml of methanesulfonic acid are added to the mixture, which is kept stirring for 1 h at this temperature. The reaction mixture is poured with stirring onto 4 l of water and of ice and the product precipitates. It is extracted with ethyl acetate (3×1 l). The combined organic phases are washed with an $NaHCO_3$ solution and then dried over $Na_2SO_4$, filtered and evaporated under reduced pressure in order to obtain 91.5 g (Yd 94%) of crude 4'-demethylepipodophyllotoxin.

Although the product can be used directly in the following synthetic operations, the product can be purified by chromatography ($SiO_2$ $CH_2Cl_2$/acetone 95/5) to provide 65% of pure 4'-demethylepipodophyllotoxin. The crude reaction product can also be purified by recrystallization from isopropyl alcohol, acetone, acetic acid or their mixture with water.

EXAMPLE 3

Use of Formic Acid 7 g (17 mmol) of podophyllotoxin I are dissolved in 3.5 ml of formic acid, one drop of methanesulfonic acid is added and the reaction mixture is stirred for 15 min at ordinary temperature, and a clear pale-yellow solution is obtained. 10.5 g (68 mmol) of D,L-methionine and 49 ml (0.63 mol) of methanesulfonic acid are then introduced with stirring and the temperature rises to approximately 400° C. over 10 min. 10.5 g of D,L-methionine are again added to the reaction mixture. After 15 min, the mixture is plunged into 500 ml of water and of ice and a precipitate is obtained which is extracted 3 times with ethyl acetate, washed with an $NaHCO_3$ solution, dried over $Na_2SO_4$ and evaporated in order to obtain 5.5 g of the compound II (Yd 81%). The product obtained is crystallized from the isopropyl ether and CH₂Cl₂ mixture in order to obtain 3.2 g of pure 4'-demethylepipodophyllotoxin (Yd 48%). Chromatography carried out on the crude reaction product (SiO₂-elution CH₂Cl₂-90-acetone-10) provides exactly the same result (3.2 g of the derivative II, Yd 48%).

EXAMPLE 4

Use of Phosphoric Acid 5 g (12 mmol) of podophyllotoxin I are added in a single step to the mixture consisting of phosphoric acid (2.5 ml), methanesulfonic acid (40 ml, 0.6 mol) and D,L-methionine (11 g, 72 mmol) cooled to 0° C. with stirring which is maintained for 6 hours with return to ordinary temperature.

The reaction mixture is then poured with stirring onto 1 l of water and of ice in order to obtain a white precipitate. It is then extracted with ethyl acetate three times and then washed with an NaHCO₃ solution. The organic phases are combined, dried over Na₂SO₄, filtered and evaporated under reduced pressure in order to obtain 4.2 g (Yd 88%) of 4'-demethylepipodophyllotoxin II. The purity of the batch obtained is 79% (HPLC analysis). The crude residue obtained can be recrystallized from solvents such as the acetone water (5/2), toluene-ethanol (90/10) or dioxane-isopropyl ether (50/50) mixture.

EXAMPLE 5

Use of a 4-chloro-4-deoxyepipodophyllotoxin Intermediate 1 g of podophyllotoxin I is dissolved in a mixture of 15 ml of CH₂Cl₂ and 5 ml of ethyl ether. A slight stream of gaseous hydrochloric acid is introduced into the solution for 15 min at –10° C. and then stirring is maintained at this temperature for 1 h. After evaporating the reaction mixture without heating, 0.54 g of D,L-methionine and then 5 ml of methanesulfonic acid are added. After dissolving and stirring for 1 h with return to ordinary temperature, the reaction mixture is plunged into a water-acetone mixture and then BaCO₃ is added to neutrality. After extracting with ethyl acetate, separating by settling, drying over Na₂SO₄, filtering and evaporating under reduced pressure, a residue is obtained which is crystallized from ethyl ether to provide 0.5 g (Yd 52%) of white crystals of 4'-demethylepipodophyllotoxin exhibiting a homogeneous spot by TLC.

EXAMPLE 6

Use of the Acetone-water Mixture

A solution of 50 g (0.12 mol) of podophyllotoxin I, prepared in 50 ml of acetone, is added with stirring at ordinary temperature to a mixture consisting of 100 g (0.67 mol) of D,L-methionine, of 500 ml (7.7 mol) of methanesulfonic acid and of 10 ml of water. The temperature rises to approximately 40° C. and stirring is maintained for 2 h with return to ambient temperature. The mixture is then poured onto ice in order to obtain a precipitate which is extracted with ethyl acetate (3×700 ml). The organic phases are washed with an NaHCO₃ solution and then separated by settling, dried over Na₂SO₄, filtered and evaporated under reduced pressure in order to obtain 4'-demethylepipodophyllotoxin, existing in the form of a white solid. 45 g (Yd 94%) are obtained.

This residue is taken up in isopropyl ether in order to obtain 38 g (Yd 80%) of 4'-demethylepipodophyllotoxin. The product thus obtained can optionally be further recrystallized from an acetone-water mixture but it can nevertheless be used directly in the subsequent synthetic stages.

EXAMPLE 7

Use of a 4-bromo-4-deoxyepipodophyllotoxin Intermediate 5 g of podophyllotoxin I are dissolved at –10° C. with slow stirring in a mixture of 100 ml of CH₂Cl₂ and 35 ml of Et₂O. A slight stream of gaseous HBr is introduced into this solution for 10 min. At this stage, the compound obtained III (R=Br) is that described by M. Kuhn, Helvetica Chimica Acta, 52, 944 (1969). The reaction mixture is then evaporated under reduced pressure without heating. 3.6 g (24 mmol) of D,L-methionine and 15.5 ml (0.24 mol) of methanesulfonic acid are subsequently introduced with stirring and the reaction is thus maintained for 2 h at room temperature. The reaction mixture is then introduced dropwise into a mixture containing equal volumes of acetone and water saturated with NaHCO₃, in order to neutralize. After stirring for 10 min, water is added and extraction is carried out with ethyl acetate, the mixture is separated by settling and the organic phases are dried over Na₂SO₄, filtered and then evaporated under reduced pressure in order to obtain 4.7 g (98%) of crude 4'-demethylepipodophyllotoxin. Chromatography on silica (elution CH₂Cl₂-acetone 90–10) provides 2.6 g of pure 4'-demethylepipodophyllotoxin (Yd 54%).

We claim:

1. Method for the synthesis of 4'-demethylepipodophyllotoxin of formula II from podophyllotoxin of formula I, which consists in treating the podophyllotoxin with a pair of reagents consisting of methanesulfonic acid, on the one hand, and dimethyl sulfide, D,L-methionine, or methylthioacetic acid, on the other hand, in the presence of water, with or without the present of a water-miscible organic solvent

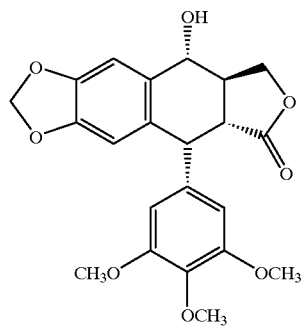

I

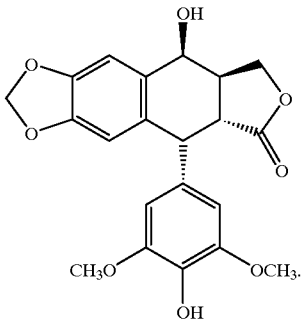

II

2. Method according to claim 1, wherein the synthesis is carried out at a temperature between about –10° C. and 40° C.

3. Method according to claim 1 wherein the compound II directly resulting from the reaction is isolated and purified by recrystallization from a solvent.

4. Method of claim 3 wherein the solvent is selected from the group consisting of isopropyl alcohol, acetic acid, water, acetone, dioxane, isopropyl ether, toluene, ethanol, and mixtures thereof.

5. Method according to claim 2, wherein the compound II directly resulting from the reaction is isolated and purified by recrystallization from a solvent.

6. Method of claim 5 wherein the solvent is selected from the group consisting of isopropyl alcohol, acetic acid, water, acetone, dioxane, isopropyl ether, toluene, ethanol, and mixtures thereof.

* * * * *

UNITED STATES PATENT AND TRADEMARK OFFICE
CERTIFICATE OF CORRECTION

PATENT NO.   : 6,008,382
DATED        : December 28, 1999
INVENTOR(S)  : Thierry Imbert and Yves Guminski It is certified that error appears in the above-identified patent and that said Letters Patent is hereby corrected as shown below:

Title page, Item [57] Abstract, line 4: "in the present"
    should read -- in the presence --.

Column 2, line 11: "sulfides" should read -- sulfide, --.

Column 4, line 60: "400°C." should read -- 40°C. --.

Column 6, line 30: "present" should read -- presence --.

Signed and Sealed this

Twelfth Day of December, 2000

Attest:

Q. TODD DICKINSON

*Attesting Officer*          *Director of Patents and Trademarks*